US010709350B2

(12) United States Patent
Skrabal et al.

(10) Patent No.: US 10,709,350 B2
(45) Date of Patent: Jul. 14, 2020

(54) BODY IMPEDANCE MEASURING DEVICE

(71) Applicant: Falko SKRABAL, Graz (AT)

(72) Inventors: Falko Skrabal, Graz (AT); Philipp Glitzner, Seiersberg (AT)

(73) Assignee: Falko Skrabal, Graz (AT)

( * ) Notice: Subject to any disclaimer, the term of this patent is extended or adjusted under 35 U.S.C. 154(b) by 92 days.

(21) Appl. No.: 15/568,333

(22) PCT Filed: Mar. 10, 2016

(86) PCT No.: PCT/AT2016/050054
§ 371 (c)(1),
(2) Date: Oct. 20, 2017

(87) PCT Pub. No.: WO2011/168873
PCT Pub. Date: Oct. 27, 2016

(65) Prior Publication Data
US 2018/0153432 A1    Jun. 7, 2018

(30) Foreign Application Priority Data
Apr. 22, 2015   (AT) .............................. A 50317/2015

(51) Int. Cl.
*A61B 5/053*         (2006.01)
*A61B 5/0428*        (2006.01)
(Continued)

(52) U.S. Cl.
CPC .......... *A61B 5/0535* (2013.01); *A61B 5/0205* (2013.01); *A61B 5/0408* (2013.01);
(Continued)

(58) Field of Classification Search
CPC ...... A61B 5/053–0537; A61B 5/04288; A61B 5/6801; A61B 2562/04
See application file for complete search history.

(56) References Cited

U.S. PATENT DOCUMENTS 6,321,112 B1   11/2001   Masuo
6,339,722 B1   1/2002   Heethaar et al.
(Continued)

FOREIGN PATENT DOCUMENTS

EP   1731092   12/2006
EP   2319411   5/2011
(Continued)

OTHER PUBLICATIONS

International Preliminary Report on Patentability of PCT/AT2016/050054, dated Oct. 24, 2017.
(Continued)

*Primary Examiner* — Thaddeus B Cox
(74) *Attorney, Agent, or Firm* — Workman Nydegger

(57) ABSTRACT

A device for impedance measurements on body segments. Outputs of a current source are connected to inputs of current changeover switches. Each current changeover switch has outputs that are interconnectable with the input of the respective current changeover switch. The outputs of the current changeover switches are connected to electric feed lines of current electrodes. Measuring electrodes detect voltage signals, which are used with the current supplied by the current source for the impedance measurements of the body segments. Switching devices are incorporated into the electric feed lines near the current electrodes. By switching the current changeover switches and switching devices, the device respectively connects only two current electrodes to the current source and disconnects all other current electrodes from the electric feed line by switching the switching device and the electric feed line from the current source by switching the current changeover switches.

15 Claims, 2 Drawing Sheets

(51) Int. Cl.
    A61B 5/0205    (2006.01)
    A61B 5/0408    (2006.01)
    A61B 5/00      (2006.01)
    A61B 5/024     (2006.01)
(52) U.S. Cl.
    CPC ........ *A61B 5/04288* (2013.01); *A61B 5/0537* (2013.01); *A61B 5/6801* (2013.01); *A61B 5/024* (2013.01); *A61B 5/04082* (2013.01); *A61B 5/7217* (2013.01); *A61B 2503/40* (2013.01); *A61B 2560/045* (2013.01); *A61B 2562/04* (2013.01)

(56) References Cited

U.S. PATENT DOCUMENTS

| | | | |
|---|---|---|---|
| 8,386,028 B2 | 2/2013 | Cha et al. | |
| 8,521,264 B2 | 8/2013 | Harrold et al. | |
| 8,548,580 B2 | 10/2013 | Chetham et al. | |
| 8,594,781 B2 | 11/2013 | Chetham | |
| 8,781,551 B2 | 7/2014 | Chetham | |
| 2006/0052678 A1* | 3/2006 | Drinan | A61B 5/0531 600/301 |
| 2006/0282005 A1* | 12/2006 | Kasahara | A61B 5/0537 600/547 |
| 2008/0009757 A1 | 1/2008 | Tsoglin et al. | |
| 2009/0030336 A1* | 1/2009 | Woo | A61B 5/0537 600/547 |
| 2009/0076345 A1* | 3/2009 | Manicka | A61B 5/0205 600/301 |
| 2010/0324404 A1 | 12/2010 | Harrold et al. | |
| 2011/0046505 A1 | 2/2011 | Cornish et al. | |
| 2011/0087129 A1 | 4/2011 | Chetham et al. | |
| 2013/0096448 A1 | 4/2013 | Brooks et al. | |
| 2013/0102920 A1 | 4/2013 | Fan et al. | |

FOREIGN PATENT DOCUMENTS

| | | |
|---|---|---|
| WO | WO2004/030535 | 4/2004 |
| WO | WO2006/063255 | 6/2006 |
| WO | WO2007/002991 | 1/2007 |
| WO | WO2008/031030 | 3/2008 |
| WO | WO2014/128237 | 8/2014 |

OTHER PUBLICATIONS

International Search Report of PCT/AT2016/050054, dated Jun. 16, 2016, PCT application filed Mar. 10, 2016.

Written Opinion of PCT/AT2016/050054, PCT application filed Mar. 10, 2016.

Skrabal et al, Medical Engineering & Physics 36 (2014) 896-904.

Skrabal F et al. Adding "hemodynamic and fluid leads" to the ECG. Part I: the electrical estimation of BNP, chronic heart failure (CHF) and extracellular fluid (ECF) accumulation. Med Eng Phys. 2014; 36:896-904.

Skrabal F et al. The Combyn™ ECG: Adding haemodynamic and fluid leads for the ECG. Part II: Prediction of total body water (TBW), extracellular fluid (ECF), ECF overload, fat mass (FM) and "dry" appendicular muscle mass (AppMM). Received Jun. 28, 2016: Med Eng Phys. 2017; 44:44-52.

Jackson AS et al. Reliability and validity of bioelectrical impedance in determining body composition. J Appl Physiol. 1988; 64(2):529-534.

Woltjer HH et al. Standardization of non-invasive impedance cardiography for assessment of stroke volume: comparison with thermodilution. Br J Anaesth. 1996; 77:748-752.

Sun SS et al. Development of bioelectrical impedance analysis prediction equations for body composition with the use of a multicomponent model for use in epidemiologic surveys. Am J Clin Nutr. 2003; 77:331-340.

* cited by examiner

BODY IMPEDANCE MEASURING DEVICE

The present application is a U.S. National Stage of International Application No. PCT/AT2016/050054, filed on Mar. 10, 2016, designating the United States and claiming the priority of Austrian Patent Application No. A 50317/2015 filed with the European Patent Office on Apr. 22, 2015. All of the aforementioned applications are incorporated herein in their respective entireties by this reference.

Recently, a new trend has emerged in the development of medical body impedance measuring devices to focus less on the measurement of body compartments by means of whole body impedance and more on measuring body compartments by means of segmental impedance measurements. Whole body impedance regards the human or animal body as consisting of different, electrically conductive body parts, and mathematical models are used to take into account different diameters and lengths of these electric conductors (i.e. arms, legs and torso). Since the resistance of an electric conductor depends, apart from its specific resistance, on its length and cross section, this method requires the assumption of fixed ratios of body size to diameters and cross sections of torso and extremities. Usually, standard proportions of the human body based e.g. on measurements on US army personnel are used for this purpose. However, these models and assumptions introduce strong inaccuracies into the method, making it suitable for approximate examinations of healthy persons, but not of ill persons.

In the segmental impedance measurement of body compartments, in particular if carried out at several different frequencies, varying dimensions of body parts and their impact on alternating-current conductance may be better taken in to account. In particular, segmental impedance measurement tries to differentiate between intracellular and extracellular water by means of multi-frequency measurements. Despite all progress in the field, it has not been possible until now to introduce these methods into standard care at the patient's bedside. One exception is the measurement of lymphedema in individual extremities or the attempt to quantify overhydration and underhydration of dialysis patients on one body part, i.e. the lower leg.

Numerous patents for segmental impedance analysis have been applied for. In the impedance measurement device proposed in WO 2007/002991 (Chetham) and in U.S. Pat. No. 8,781,551 (Chetham), for example, the measuring current is measured and then readjusted, but no changeover switching options are provided. U.S. Pat. No. 8,594,781 (Chetham) discloses an impedance measurement device in which measuring electrodes are disconnected in order to reduce inductive coupling. In the impedance measurement device according to US 2011/0087129 (Chetham), a first system determines the impedance procedure, selects instructions, a second system generates control signals according to these instructions. In U.S. Pat. No. 8,548,580 Chetham suggests two systems, the first of which selects instructions for the measurement and transfers the instructions to a second system. US 2008/0009757 A1 (Tsoglin) discloses an impedance measurement device in which current distortions in sections of the body that are not probed are considered utilizing an electrical model that seems to correspond to the Kirchhoff's laws. In U.S. Pat. No. 8,386,028 Cha examines two segments simultaneously at two different frequencies. US 2011/0046505 (Cornish) compares two different body segments with each other.

WO 2008/031030 (Bartnik) discloses the calculation of systolic time intervals by subtracting a second waveform, obtained from echocardiography or a pulse wave or a pulsoxymeter, from a first waveform, obtained from an impedance signal. WO 2006/063255A2 (Bernstein) discloses the determination of the stroke volume from the impedance signal over the thorax or the brachial artery. US 2013/0096448 (Brooks) describes a combined ECG (electrocardiography), ICG (impedance cardiography) and phono electrode on one common carrier with an acoustic chamber. The documents U.S. Pat. No. 8,521,264 and US 2010/0324404 describe the use of no more than three combined ECG/ICG electrodes all placed on the thorax. U.S. Pat. No. 6,339,722 (Heethaar) suggests measuring the thorax as one segment with two frequencies and with two different measuring distances in order to obtain information about heart activity.

In order to carry out a multi-frequency impedance analysis in a quick and simple manner it is necessary to measure numerous body segments automatically and appropriately without intervention by the user. In general, a multiplexer integrated into the device is provided for this purpose. Multiplexers for impedance measurements are sometimes used in impedance measurement devices cited above in order to feed in current at different body sites and to measure voltages at different body sites.

However, this entails several problems that were not considered in the documents cited above. In many applications, the distance between the measurement device and the examined body has to be kept large, which also entails relatively large cable lengths. This may lead to essential difficulties and errors during measurements. Thus, cables and their shieldings may create parasitic capacitances and inductivities. Studies carried out by the applicants have shown that it is particularly important to avoid parasitic leakage currents flowing through cables simultaneously attached to the body, which are not provided for current input at the time of use. In addition, it is to be avoided that due to the combination of feeding and measurement cables, which result in numerous feeding and measurement points, stray impedances and stray capacitances cause distortions of the signals measured in the individual cables.

It is thus an object of the present invention to create a device avoiding these problems and disadvantages of the state of the art.

The present invention solves this problem by means of a device with the characteristics according to claim 1. Advantageous embodiments of the invention are described in the subclaims.

The inventive device for impedance measurements on segments of a human or animal body, the impedance measurements preferably being multi-frequency impedance measurements, comprises a current source, current changeover switches, current electrodes and measuring electrodes arrangeable on segments of a human or animal body. Each output of the current source is connected to an input of a current changeover switch, each current changeover switch having a plurality of outputs and the input of a respective current changeover switch being switchably interconnectable with one of its outputs, wherein the outputs of the current changeover switches are connected to electric feed lines of the current electrodes. The measuring electrodes detect voltage signals, and the device determines impedances of segments of the human or animal body based on the current provided by the current source and the detected voltage signals. The feed lines have integrated switching devices near or directly at the current electrodes, which integrated switching devices allow connecting and disconnecting the current electrodes and their feed lines. The device is configured to connect only two current electrodes to the current source at a time by switching the current changeover switches and the switching devices in order to separate all other current electrodes from the feed line by switching the switching device and to separate the feed line from the current source by switching the current changeover switches.

Preferably, voltage amplifiers or voltage followers with high input resistances are integrated into the signal lines near to or directly at the measuring electrodes.

For automatic measurements, the switching devices should be implemented to be switchable by the device.

For the automatic measurement of impedances on different body segments, the invention provides in one embodiment that signal lines of the measuring electrodes lead to inputs of voltage changeover switches, the voltage changeover switches each having an output that is interconnectable with an input of the voltage changeover switch. This configuration allows easier impedance measurements because the outputs of the voltage changeover switch are connected to inputs of a differential amplifier, which determines a differential voltage from the voltage signals at its inputs, which differential voltage the device uses for impedance determination.

High reliability and quick measurements are achieved by implementing the current changeover switches and/or the voltage changeover switches as relays or multiplexers.

The measurement results are substantially improved when the device according to the invention is provided with common mode rejection. According to the invention, it is provided that a compensating current may be applied to at least one of the current electrodes via a resistor, wherein the connection of the resistor to the current electrode is positioned between the switching device and the current electrode. Alternatively or additionally, a compensating current electrode is provided, to which a compensating current may be applied via a resistor.

Handling of the inventive device becomes particularly easy for the examination personnel when, apart from optional single measuring electrodes, one current electrode and one measuring electrode, respectively, are grouped into a combined electrode region. Handling of the device is even easier when the current electrode and the measuring electrode of the combined electrode region have their feed lines and signal lines routed together because in this case only half the number of cables has to be handled. A further simplification of handling is based on the fact that the current electrode and the measuring electrode are arranged on a common electrode carrier. The common electrode carrier is preferably a clip, a belt, a cuff, or a pressure cuff (similar to the pressure cuffs used for blood pressure measurements). When a clip, cuff or pressure cuff is used, a pressure sensor for pulse measurement may additionally be arranged thereon. It is advantageous for the implementation of automatic measurements if the pressure sensor has a liquid-filled balloon communicating with a pressure transducer, wherein preferably the liquid-filled balloon is pressable against a body part by means of a controlled, hydraulically or electric motor-driven pressing device.

It has been shown that the accuracy of measurements is substantially improved when the device interconnects the current electrode of no more than one combined electrode region with the current source and uses the measuring electrode for voltage measurements. In this regard, it has proven to be advantageous when combined electrode regions are selectable for attachment to peripheral body segments and central body segments, wherein optionally a further combined electrode region is selectable for attachment to a body region where the chest wall electrodes V1 to V6, preferably V4 to V6, of an ECG are placed. In the simplest application, however, only one of the chest wall electrodes V1 to V6, preferably V4 to V6, has to be used as measuring electrode for the impedance measurement.

In addition, it is convenient if the device is provided with a differentiator for determining impedance changes with the heartbeat.

In a preferred embodiment of the inventive device, an ECG device is integrated into the device, wherein the ECG device has at least extremities electrodes, preferably also chest wall electrodes. This allows carrying out impedance measurements and ECG recordings simultaneously by means of the inventive device. To minimize the number of electrodes that have to be placed on the body, the invention also suggests that the measuring electrodes are implemented as ECG electrodes by providing branch lines of the signal lines of the measuring electrodes to the ECG device.

When the current electrodes and/or the measuring electrodes are implemented as transducers and/or generators for physical quantities, in particular acceleration values, pressure, sound, temperature, or light, other physical quantities and parameters may also be measured during impedance measurements. Reliable measurements and easy handling are achieved by implementing at least some of the current electrodes and the measuring electrodes as suction electrodes or adhesive electrodes.

Below, the invention will be explained in further detail by means of exemplary embodiments and with reference to the drawings.

Figure 1:
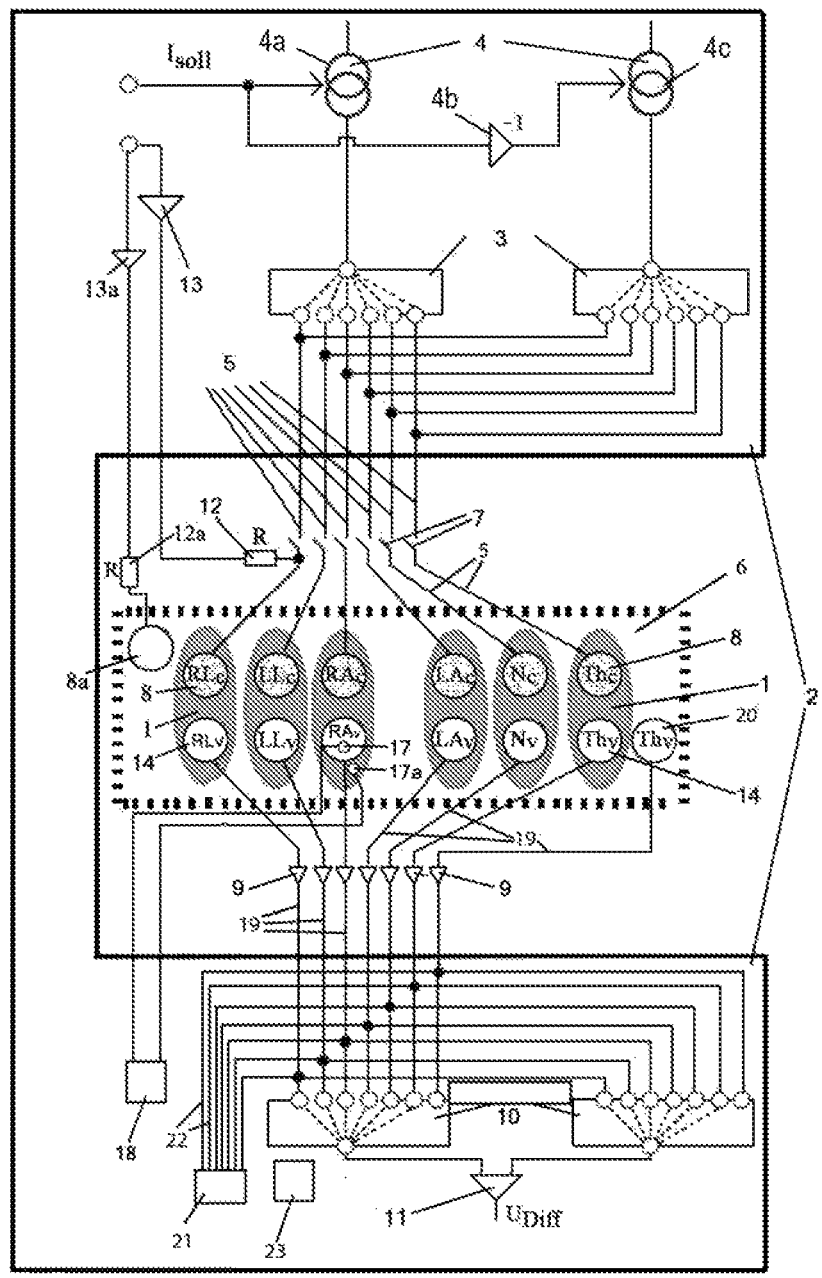
FIG. 1 shows a schematic block diagram of the inventive device.
Figure 2:
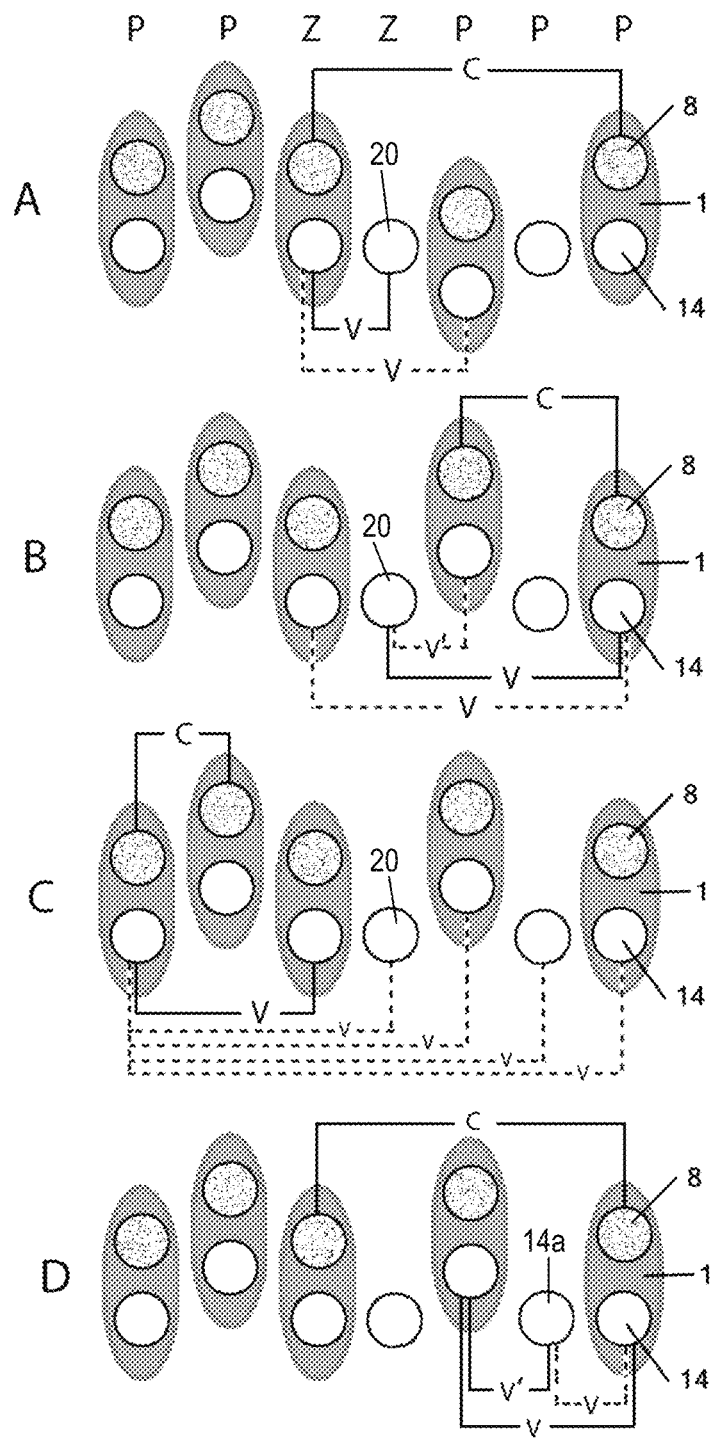
FIG. 2 shows application examples of the inventive device.

The following description refers to FIG. 1 and FIG. 2. For clarity, equal parts with equal configurations that are shown several times next to each other have been assigned only one reference number in those two figures.

FIG. 1 shows a schematic block diagram of the device 2 according to the invention for measuring impedances of segments of a human or animal body. The device 2 comprises a current source 4 having two partial current sources 4a, 4c with opposite polarity controllable by a control current Isoll, wherein the control current Isoll flows through an inverter 4b on its way to one of the partial current sources 4c before entering the partial current source 4c. The output of each partial current source 4a, 4c is connected to the input of a current changeover switch 3, which is e.g. implemented as a multiplexer. Each current changeover switch 3 has a plurality of outputs, its input being switchably interconnected with one of the outputs. The outputs of the current changeover switches 3 are connected to current electrodes 8 via electric feed lines 5. The current electrodes 8 are shown with a dotted surface. Current electrodes 8 are attached to individual body segments of the individual being examined (human or animal). The surface of the individual 6 being examined is shown symbolically by means of a dashed line in the Fig. Near the current electrodes 8, switching devices 7 are integrated into the feed lines 5, with which switching devices 7 the current electrodes 8 may be connected to and disconnected from a feed line 5. This serves to make sure that no parasitic leaking currents may flow from the current electrodes 8 to the device 2 during operation of device 2, wherein the switching devices 7 make sure that in the disconnected state, the current electrodes 8 are separated from the feed lines 5. The switching devices 7 may be implemented as mechanic switches (e.g. microrelays), electronic switches, or negative impedance converters. Thus, every feed line 5 is, on the one hand, disconnected from the current source 4 via the current changeover switch 3 within the device 2, and, on the other hand, additionally disconnected from the current electrode 8 a second time via the switching device 7 peripherally to the device 2, which avoids parasitary leaking currents that could flow from the periphery through the body of the individual into the cables of feed lines 5. This is particularly important because the cables of feed lines 5 should advantageously be shielded and—in order to provide an even better shielding effect—be provided with an active shielding. However, due to this an alternating current generated by the capacitances between cable and shielding may flow, which is prevented by the switching devices 7.

The exemplary embodiment of FIG. 1 provides for six current electrodes 8. The first four current electrodes 8 are examples of current feeds at the right leg (RLc refers to right leg current), at the left leg (LLc refers to left leg current), at the right arm (RAc refers to right arm current), and at the left arm (LAc refers to left arm current). The fifth current electrode 8, which may optionally be attached, is to be placed at the thoracic aperture, e.g. near the upper sternum, at the neck or at the head, for feeding current (Nc refers to Neck current). The sixth current electrode 8 serves for feeding current at the lower end of the thorax (referred to as Thc), e.g. in the region where the leads V4 to V6 or V4r to V6r are placed for an ECG.

Each current electrode 8 is assigned to a measuring electrode 14, the current electrode 8 and the measuring electrode 14 not being electrically interconnected, and the combination of current electrode 8 and measuring electrode 14 is arranged on the individual 6 in a so-called combined electrode region 1. The distance between the electrodes 8, 14 of the combined electrode region should be at least 2 cm to 4 cm, better not less than 3 cm to 4 cm and not more than 20 to 30 cm. In the exemplary embodiment of FIG. 1 there are thus, for example, six combined electrode regions 1 with one current electrode 8 and one measuring electrode 14 each as well as with at least one additional measuring electrode 20.

The measuring electrodes 14 are marked as RLv for right leg voltage, LLv for left leg voltage, RAv for right arm voltage, LAv for left arm voltage, Nc for neck voltage, and Thv for thorax voltage. Each measuring electrode 14 may be arranged together with the associated current electrode 8 on a suitable common electrode carrier, e.g. a clip electrode, an adhesive electrode, a suction electrode, a belt electrode, a cuff electrode or a pressure cuff electrode. Alternatively, the measuring electrodes 14 and current electrodes 8 are provided as separate individual electrodes.

The measuring electrodes 14 are connected to signal lines 19, which lead to inputs of two current changeover switches 10, wherein voltage amplifiers 9 are provided in the signal lines 19. The voltage amplifiers 9 may be implemented as voltage followers with high input resistance. The voltage amplifiers 9 should be positioned as close as possible to or at the measuring electrodes 14. The voltage changeover switches 10 are for example implemented as relays or electronic voltage multiplexers. By means of the voltage changeover switches 10, signals of a measuring electrode 14 may be switched to the outputs of the voltage changeover switches 10 one by one, where they are e.g. introduced into the input of a differential amplifier 11 for further processing. The output signal UDiff of the differential amplifier is the difference between the output signals of the two voltage changeover switches 10.

Another important precondition for the device 2 to function optimally is the provision of common mode rejection because there is high electromagnetic interference from the examined individual 6. Alternating current interference, caused by the voltage supply network, may also cause enormous disturbances. In addition, maladjustments between the individual cable capacitances and cable impedances of the feed lines 5 and signal lines 19 have to be balanced. In addition to conventional methods for optimally shielding the cable, also by using active shielding or special signal filtering techniques, such as adaptive filters or notch filters, the common mode voltage needs to be balanced by sending a compensating current through a high resistor 12 with a resistance value between 470 kOhm and 1.5 MOhm, preferably 1 MOhm. However, for this a terminal of the resistor 12 must be connected via at least one of the feed lines 5 to the current electrodes 8, between the switching device 7 and the current electrode 8. The other terminal of the resistor 12 is connected to the output of an operational amplifier 13, which provides the compensating current. The resistor 12 is advantageously placed near the current electrode 8 used for feeding the compensating current. Each of the current electrodes 8 is suitable for feeding the compensating current. Alternatively or additionally, a dedicated compensating current electrode 8a may be provided, which is connected via a resistor 12a (between 470 kOhm and 1.5 MOhm, preferably 1 MOhm) to the output of an operational amplifier 13a, which provides the compensating current as known.

A device 2 with such a configuration allows an automatic examination of numerous segments of the individual 6. On the one hand, it is possible to generate alternating currents with any frequency by means of the control signal Isoll and the two inversely operated partial current sources 4a, 4c and to send them to freely selectable current electrodes 8 by means of the two current changeover switches 3. On the other hand, voltage signals from freely selectable measuring electrodes 14 may be selected for further processing, in particular for the creation of differences at the differential amplifier 11, by means of the two voltage changeover switches 10. The control of the control signal Isoll, of the current changeover switches 3, of the voltage changeover switches 10, the mathematical processing of the voltage signals determined by the measuring electrodes 14, as well as control of all other functions of the device is carried out by a CPU 23 installed in the device 2, which CPU may e.g. be implemented in the form of a microcontroller. The required numerous supply lines leading to the CPU 23 are not shown for reasons of clarity.

It is thus possible to carry out automatic impedance measurements with different frequencies on different segments of the individual 6 by means of device 2. Based on these impedance measurements on different body segments, the device 2 also offers the possibility of impedance cardiography (ICG).

In addition, the CPU 23 in the device 2 can, based on impedance measurements and on stored empirical equations or on predefined mathematical models, calculate the body composition of the entire body of the individual 6 and of its body parts, such as body water contained in body parts, extracellular liquid, muscle mass, fat mass, their deviations from nominal values, as well as edemas or accumulations of water in body parts, and output the calculated results for display on a screen, storage in a non-volatile storage or further processing in a data bank. It is to be appreciated that a doctor can diagnose a deviation of hydration from the norm, e.g. deviations of the ratio between fat mass or "lean body mass" and extracellular volume or the ratio between extracellular and intracellular volume or whole body water, by means of device 2, and thus determine overhydration or dehydration in an easier manner. Furthermore, arterial circulatory disorders, in particular of the legs or their segments, can be identified and output. This allows the calculation of an "ankle brachial index" (ABI), as known from the literature, based on the acceleration difference between the volume of the legs and the heartbeat. The impedances determined with the device 2 as well as their effective resistance and reactance portions and the impedance phase angle are used for the development of regression equations by means of multiple regressions or neuronal networks in order to estimate parameters relevant to the physician and to predict parameters determined by means of gold standard practices such as whole body DXA, deuterium dilution, sodium bromide dilution, or other tracers.

When device 2 additionally differentiates the determined impedance signals and relates them to the heartbeat, the calculated changes of the impedance with the heartbeat may be used to measure the acceleration of blood in different body parts. This is particularly useful when carried out in one segment, defined on the one hand by a central combined electrode region (e.g. positioned on the neck, the nape or the shoulders) and on the other hand by a further central single electrode (e.g. selected from V4 to V6 or from V4r to V6r) and a peripheral combined electrode region and a central and a peripheral combined electrode region, as described in Skrabal et al, Medical Engineering & Physics 36 (2014) 896-904. In this regard it is only essential that at least one measuring electrode 14 is positioned between two current electrodes 8. This allows not only the determination of cardiac output and the diagnosis of cardiac insufficiency, but also the measurement of arterial and venous circulation or pulse transit time (volume transit time). Again, preferably gold standard methods such as echocardiography and other hemodynamic methods such as ankle brachial index, pulse transit time, pulse wave analysis with augmentation index, central and peripheral compliance, stroke volume from pulse curve may be used as gold standard methods for calibrating the new methods.

Device 2 may also have an integrated ECG device 21. This ECG device 21 may be equipped with separate ECG electrodes, which are not shown in FIG. 1 for reasons of clarity. A special advantage of device 2 is the possibility to implement the measuring electrodes 14 as ECG electrodes by providing branch lines 22, preferably between voltage amplifiers 9 and voltage changeover switches 10, leading from the signal lines 19 of the measuring electrodes 14 to the ECG device 21. Thus, device 2 may serve as a multi-channel ECG device and simultaneously carry out the described impedance measurements and calculations based on the determined impedances while it records multi-channel ECGs. Because recordings over a certain time, e.g. 2 to 3 minutes, are advantageous for obtaining templates, a rhythm strip is also generated automatically as desirable and common for general ECG. This also allows a spectral analysis of cardiac intervals and impedance changes with the heartbeat. Based on the corresponding frequency bands, e.g. the 0.1 Hz band and the 0.3 Hz band, the portions of the sympathetic and vagus nerves in controlling the heart rate may be determined, which is especially suitable for determining overtraining, burnout, depression, etc., in particular if traceable over time for several weeks or months. All this does not require more time than general rhythm strips for ECG.

The invention also provides for the attachment of sensors or actuators to the current electrodes 8 or measuring electrodes 14, e.g. accelerometers, pressure sensors, or light sensors, LEDs, or pressure pumps. FIG. 1 schematically shows a measurement value transducer/generator 17 lying directly underneath an electrode (current or measuring electrodes may be used), which may optionally also be implemented as a measurement value transducer/generator 17a next to the electrode. The measurement value sensor 7 and/or generator 17, 17a are controlled by an evaluation unit 18, which in this case also acts as a generator for the measurement value to be input, e.g. a pressure signal. The transducer/generator 17, 17a is connected to an input of the evaluation unit 18, which evaluates the received measurement value, e.g. a pressure signal, an acceleration signal, a temperature signal, etc. With sensors as described above, the device 2 can implement impedance measurements and ECG recordings simultaneously with the recording of other circulation parameters, such as circulation times, pulse wave analyses including heart stroke volume, pulsoximetry, etc., corresponding methods being disclosed in detail in WO 2004/030535 A1 (Skrabal) and EP 2319411 A2. The pulse wave analysis may then also be used for calculating other parameters such as vessel stiffness, augmentation index, central aortic pressure, stroke volume, etc. The optional placement of blood pressure cuffs is provided for as well, also at the lower extremities for determining the ankle brachial index and for venous occlusion plethysmography.

The device 2 is thus a measurement device that, at its fullest extension level, does not only carry out impedance measurements on several body segments of a human or animal body at several or numerous impedance frequencies, but optionally also comprises a differentiator (which may be integrated into CPU 23) for detecting impedance changes with the heartbeat. The heartbeat may be determined accurately by ECG so that thereafter a time window for searching for impedance changes with the heartbeat may be determined. Templates are generated from the different segments for impedance cardiography and impedance rheography. The measurement device is optionally also a (multi-channel) ECG device and serves as analyzing device for further physical quantities, as long as corresponding sensors and actuators are integrated into the electrodes.

FIG. 2 shows the application of the principle of partially or completely separating the combined electrode regions 1 during current feeding (C for current) via the current electrodes 8 and during voltage measurements (V for voltage) via the measuring electrodes 14 of the device 2 by means of four examples A, B, C, D. As shown, these examples use the combined electrode regions 1 for current feeding on the one hand and for voltage measurements on the other hand in partially or totally different manners. The current electrodes are shown with a dotted surface, the measuring electrodes are white. When an electrode pair is anatomically positioned outside the electric circuit, it is also displaced in the drawing and drawn outside of the electric circuit.

In one embodiment of the invention, the device determines the impedance and impedance changes with the heartbeat in at least two body segments, the segments being defined as follows.

a) On the one hand, the central segment with regard to current feeding is defined by the current electrodes 8 of a central (Z) combined electrode region 1 and a peripheral (P) combined electrode region 1, while the measuring section is defined by the measuring electrode 14 of the central combined electrode region 1 and by a measuring electrode 20, which is also used as a lead in chest wall ECG. (FIG. 2-A, drawn-through measuring section V.) Another central combined electrode region 1 could be used, though less comfortably, the measuring electrode 14 of which is used for measuring the impedance and the current electrode 8 of which is used for feeding current (not shown). Alternatively, the measuring section V could, at the same feeding conditions, be defined by the measuring electrode 14 of the central combined electrode region and by the measuring electrode 14 of a combined electrode region that is not positioned within the electric circuit (e.g. positioned at the contralateral leg). (See dashed measuring section in FIG. 2A).

b) On the other hand, the peripheral body segment of current feeding is defined by the current electrodes 8 of two peripheral combined electrode regions (e.g. positioned on the legs), while the measuring section is defined by one measuring electrode that is positioned outside of the electric circuit (e.g. ECG electrode 20 positioned above the chest wall) and the measuring electrode 14 of the combined electrode region 1, which was also used for feeding current (FIG. 2-B, drawn-through measurement circle). Alternatively, the measurement circle could under the same feeding conditions be defined by a measuring electrode 14 positioned outside the electric circuit of a central combined electrode region and by the measuring electrode 14 of the electrode region used for feeding current (FIG. 2-B, dashed measuring section). In analogy to these embodiments, a further segment between the central single electrode 20, which could correspond to a ECG chest wall electrode, and the measuring electrode 14 of another combined electrode region, which does not carry any current, could be analyzed (see dashed line V'). This could e.g. be the abdominal segment.

c) FIG. 2-C shows a similar measurement arrangement to FIG. 2-B with which a further peripheral body segment may be measured. This could e.g. be the arms. This drawing illustrates how many different measurement points may be used, as long as they are outside of the electric circuit. This is of course also true for the other drawings 2-A, 2-B, 2-C, where they are not shown for reasons of clarity. However, current should be fed so that no two body segments with pulsatile changes of the volume simultaneously carry a current and are measured at the same time because the pulsatile components would mix up. It would be possible, though with enormous efforts, to calculate the pulsatile components of two segments.

d) FIG. 2-D shows a measurement arrangement which also allows measuring partial segments of a peripheral body segment if additional single measuring electrodes 14a are arranged between peripheral and central electrode pairs. The shown measurement segment V serves for measuring the entire segment, the shown measurement segment V' serves for measuring the proximal part, and the segment with the dashed line serves for measuring the peripheral body segments.

In line with the innovation, in all drawings of FIG. 2 only one measuring section at a time is opened up by the voltage changeover switch 10, feeding is preferably also carried out only in the segment that is examined, while all other segments are disconnected via the additional switching devices 7 and the current changeover switch 3.

Thus, any body segment may be measured with regard to the impedance as well as impedance changes with the heartbeat by carrying out a minimum of current changeover switchings. It will be obvious to a person skilled in the art that only a fraction of all possible alternatives that this changeover switching system offers is shown and that its application is not limited to the electric and voltage circuits shown in the drawings.

The essential aspect of impedance measurements of the device 2 is that of all combined electrode regions 1 only the current electrode 8 for feeding current as well as the measuring electrode 14 for voltage measurements of one combined electrode region are used. With all other combined electrode regions either only one of the two electrodes 8, 14 or none of the two electrodes 8, 14 are used.

Regarding the implementation of the electrodes 8, 14, it is advantageous for handling if at least some of them are implemented as suction electrodes, clip electrodes, adhesive electrodes, belt electrodes, cuff electrodes, or pressure cuff electrodes. They may be configured as spot electrodes, strip electrodes or double strip electrodes, with double strip electrodes having shown to be effective if they are not parallel but arranged in various angles towards each other. The electrodes, in particular adhesive electrodes, which are usually disposable electrodes, may also be used to be identified e.g. by means of RFID or other aids. It is thus possible, for the purpose of achieving accurate measurement results, to only allow the use of electrodes with which the device was originally calibrated and which thus guarantee the necessary quality and configuration.

In sum, the device 2 according to the invention allows impedance measurements of body segments at several frequencies, if suitable also by use of a Cole-Cole plot, for determining intracellular water (e.g. muscle mass and fat mass) as well as extracellular water, and also impedance measurements where the body is divided into various segments, e.g. arms and legs (or only segments of arms and legs), thorax and its parts, i.e. thorax and abdomen (since they have very different compositions and thus different specific resistances). This is possible by using as few feed lines 5 to the body and as few electrodes 8, 14 on the body of the individual 6 as possible. The present device 2 may use the so-called 4-point method with current electrodes 8 positioned outside or in the vicinity, and measuring electrodes 14 positioned inside or in the vicinity.

The combined electrode regions 1 are provided for attachment to different body parts so that peripheral electrode regions (at the end of extremities of living bodies) and central electrode regions (at the thorax, neck, head area) may be distinguished.

Peripheral combined electrode regions are positioned on:

a) Fingers, hands, lower arms for feeding current and measuring voltages (e.g. feeding at finger, hand and hand and lower arm, respectively, for voltage measurement on the left and right upper extremity).

b) Toes, feet, lower legs for feeding current, and feet and lower legs for measuring voltages on the left and right lower extremity, respectively.

Central combined electrode regions are positioned on:

c) Head, neck, upper chest for feeding current and for measuring voltages, respectively. In this area, only one electrode might suffice for voltage measurements.

d) Lower chest for feeding current and measuring voltages, wherein in this area electrodes for voltage measurements might suffice.

Other regions of the body, which may be subjected to a similar measurement approach, e.g. also localized body regions such as parts of the head, the neck, the chest, the abdomen or the mamma may also be selected for attaching combined electrode regions.

The above explanations show clearly how complex and diverse the design and functioning of device 2 are. Therefore, the implementation of the current changeover switches 3 and voltage changeover switches 10 as multiplexers has proven of value. The use of a FPGA in the design of switches also entails enormous simplifications. In order to integrate a multi-channel ECG into the measurements, the CPU 23 must have large calculating capacities and thus be implemented as a fast processor, while the data storage also needs to be large and fast. For visualizing the measurement results, a large screen for displaying the numerous synchronized data and curves should be provided. Interfaces with existing medical systems could be provided. Data should be provided in data formats, e.g. Excel or other data bank formats, suitable for scientific analyses. A data storage by means of which changes of body composition, body functions and of the ECGs of individual patients over time may be registered and output numerically and/or graphically has proven useful. By using empirical formulas, which are calibrated by means of gold standard methods (e.g. echocardiography, biochemical parameters such as NTpro-BNP or its derivatives or other biochemical parameters that change with heart insufficiency, ergometry, spiroergometry, oxygen uptake thresholds, lactate measurements, ankle brachial index, arteriography, whole-body DXA, deuterium and sodium bromide determinations), body functions and compositions, such as cardiac performance, cardiac fiber elongation, maximum performance, its threshold, arterial and venous circulation, muscle mass, fat mass, whole-body water, extracellular space and their deviations from the norm, may be determined by estimating the above parameters, e.g. by means of multiple regression equations, which might comprise anthropometric data and all impedance data, based on gold standard methods. For determining over- or under-hydration and sarcopenia it has proven advantageous to calculate deviations of TBW or ECW or ICW or ECW/ICW ratios from regression levels between FM/kg body weight, on the one hand, and TBW/kg body weight or ECW/kg body weight or ECW/ICR, on the other hand, determined in healthy individuals. For determining sarcopenia, the output of "appendicular muscle mass" according to the international standard, i.e. muscle mass of the shoulders and arms or of the hip and legs, and as excellently recorded by segmental impedance spectroscopy, has proven useful. The correction of a muscle mass thus calculated via correction of an at best disturbed ratio (e.g. quotient) between extracellular space and intracellular space or whole-body water has also proven useful. By this means, the presence of sarcopenia and its grading compared to a norm-collective may be output.

Also particularly interesting is the output and/or graphic representation of variations in time of determined parameters, not only after single interventions such as ergometry, pacemaker settings, pharmacological and physiological interventions, not only in single examinations, but in particular in repeated examinations at larger time intervals. In this connection, only variations in time may be selected, e.g. automatically, where the measured or calculated parameters changed significantly and in to clinically relevant extent compared to the last recording. Clinically relevant are e.g. changes of parameters exiting the known normal range, e.g. PQ interval, development of an AV block, QT duration above or below the frequency-adapted normal range, changes of cardiac vectors, amplitude and direction of T wave, sudden changes of heart rate, sympathovagal balance, calculated from the power of the 0.1 and 0.3 Hz bands or from the ratio between the 0.1 and 0.3 Hz bands of heart rate variability, sudden interim differences between segments, volume wave in the legs, or increases of ECF/ICF or ECF/TBW ratios in single body segments etc. This avoids unclear prints of their development.

The invention claimed is:

1. Device for impedance measurements on segments of a human or animal body, the impedance measurements being multi-frequency impedance measurements, wherein the device comprises a current source, current changeover switches, current electrodes placeable on segments of the human or animal body, voltage changeover switches and measuring electrodes, wherein each output of the current source is connected to an input of a current changeover switch, wherein each current changeover switch has a plurality of outputs and the input of the respective current changeover switch is switchably interconnectable with one of its outputs, wherein each of the outputs of the current changeover switches is connected by an electric feed line to one of the current electrodes, wherein each voltage changeover switch has a plurality of inputs and an output and the output of the respective voltage changeover switch is switchably interconnectable with one of its inputs, wherein each of the inputs of the voltage changeover switches is connected by a signal line to one of the measuring electrodes, wherein the measuring electrodes detect voltage signals and the device determines the impedances of the segments of the human or animal body from the current supplied by the current source and the detected voltage signals, wherein switching devices are incorporated into each of the electric feed lines at the current electrodes, with which switching devices each of the current electrodes may be connected to or disconnected from its electric feed line, wherein the device is configured to always open up only one measuring section via the voltage changeover switches and respectively connect only two current electrodes to the current source by switching the current changeover switches and the switching devices, while all other current electrodes are disconnected from their electric feed lines by switching the switching devices, and to disconnect the electric feed lines from the current source by switching the current changeover switches.

2. Device according to claim 1, wherein voltage amplifiers or voltage followers with a high input resistance are integrated into the signal lines at the measuring electrodes.

3. Device according to claim 1, wherein the switching devices are switchable by the device.

4. Device according to claim 1, wherein the outputs of the voltage changeover switches are connected to inputs of a differential amplifier, which, based on the voltage signals applied to its inputs, determines a differential voltage (Udiff), which the device uses for the determination of impedance.

5. Device according to claim 1, wherein a compensating current may be applied to at least one of the current electrodes or an additional electrode via a resistor, wherein the connection of the resistor to the current electrode is positioned between the switching device and the current electrode.

6. Device according to claim 1, wherein a compensating current electrode is provided, to which a compensating current may be applied via a resistor.

7. Device according to claim 6, wherein combined electrode regions are selectable for attachment to peripheral body segments and central body segments, wherein a further combined electrode region is selectable for attachment to a body region where chest wall electrodes V1 to V6 of an ECG are placed.

8. Device according to claim 1, wherein one current electrode and one measuring electrode, respectively, are arranged on a common electrode carrier grouped into a first combined electrode region, wherein current feeding always takes place with two current electrodes that are respectively grouped in a second combined electrode region, wherein, however, not more than one measuring electrode is used at a time, which is positioned on one of the first or second combined electrode regions.

9. Device according to claim 8, wherein the device interconnects the current electrode of no more than one combined electrode region with the current source and uses the measuring electrode for voltage measurements.

10. Device according to claim 9, wherein a pressure sensor for pulse measurement is arranged on the common electrode carrier, the pressure sensor comprising a liquid-filled balloon communicating with a pressure transducer, wherein the liquid-filled balloon is pressable against a body part by a controlled hydraulic-driven or electric motor-driven pressing device.

11. Device according to claim 1, wherein the device is operable to determine the impedance and impedance changes, with a heartbeat, of two body segments, the body segments being defined: a) with regard to feeding by two combined electrode regions positionable on a central (Z) body part and a peripheral (P) body part, and with regard to voltage measurements by a combined electrode region positionable on a central (Z) body part and a centrally positioned single electrode; and b) regarding current feeding by two electrode regions positionable on peripheral (P) body parts, and with regard to voltage measurements by a peripheral (P) combined electrode region and a central measuring electrode, either as single electrode or as measuring electrode of a central (Z) combined electrode region, or c) with regard to current feeding by a central (Z) and a peripheral combined electrode region, and with regard to voltage measurements by two peripheral (P) combined electrode regions, one of which does not carry any current.

12. Device according to claim 1, wherein an ECG device is integrated into the device, and wherein the ECG device has extremities electrodes and chest wall electrodes.

13. Device according to claim 12, wherein the measuring electrodes are implemented as ECG electrodes by providing branch lines of the signal lines of the measuring electrodes to the ECG device.

14. Device according to claim 1, wherein the current electrodes and/or the measuring electrodes are implemented as transducers/generators for acceleration values.

15. Device according to claim 1, wherein the device has a CPU that, by use of multiple regression equations or mathematical models, is operable to determine parameters of body functions and compositions, comprising cardiac performance, biochemical parameters thereof, for physical maximum performance, for aerobic and anaerobic thresholds, for circulation of body parts, for arterial and venous functions including ankle brachial index, arterial and venous thromboses or arterial embolisms, body compartments, whole-body water, extracellular space, muscle mass, fat mass, ratio between extracellular space and intracellular space or total-body water in a whole body and in individual body parts and their deviations from a norm.

* * * * *